United States Patent Office

Plant Pat. 1,962
Patented July 26, 1960

1,962

ROSE PLANT

Dennison H. Morey, Jr., Pleasanton, Calif., assignor to Jackson & Perkins Company, Newark, N.Y., a corporation of New York Filed Oct. 19, 1959, Ser. No. 847,440

1 Claim. (Cl. 47—61)

The present invention relates to a new and distinct variety of rose plant of the floribunda class, which was originated by me by crossing the variety "Charlotte Armstrong" (Plant Patent No. 455) with the variety "Independence" (Plant Patent No. 1,036).

The primary objective of this breeding was to produce a new rose variety of the floribunda class which bears flowers of a color falling in the Coral Orange range. This objective was fully achieved, along with other desirable improvements, as evidenced by the following unique combination of characteristics which are outstanding in the new variety and which distinguish it from its parents, as well as from all other varieties of which I am aware:

(1) An unsual and attractive contrast of foliage and flower color;

(2) Relatively large flower size (larger than previous floribundas);

(3) An interesting and distinctive sepal arrangement, with the sepals forming a hood over the bud, with one sepal unusually broad and serrated, and the other sepals deeply serrated; and (4) A distinctive and attractive Geranium Pink, lightly overcast with Scarlet-Red general color tonality of the flowers.

Asexual reproduction of the new variety by budding, as performed at Pleasanton, California and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Charlotte Armstrong."
*Pollen parent.*—"Independence."

Classification:
*Botanic.*—Floribunda.
*Commercial.*—Floribunda.

*Flower*

(Observations made from specimens grown outdoors at Newark, New York, in the late morning during the latter part of June.)

Blooming habit: Recurrent—continuous.

Bud:
*Size.*—Large.
*Form.*—Pointed; ovoid; is not affected by wet or hot weather.
*Color.*—When sepals first divide—Oxblood Red, Plate 1. When petals begin to unfurl—Scarlet-Red, Plate 1, lightly overcast with Rose Doree, Plate 1. When half-blown: inside of petals—Rose Doree, Plate 1; reverse of petals—Rose Doree, Plate 1, lightly overcast with Scarlet, Plate 1.

*Sepals.*—Serrated; branched ("hood" above bud); stand up when petals begin to unfurl. Color: inside—Chromium Green, Plate 32, with edge lightly overcast with Eugenia Red, Plate 13; outside—Light Cress Green, Plate 31, with upper half of sepal lightly overcast with Carmine, Plate 1.
*Calyx.*—Color—Light Bice Green, Plate 17. Shape — Pear. Size — small. Aspect — smooth. Odor when rubbed—none.
*Peduncle.*—Length — medium. Aspect — rough. Strength—erect; slender. Color—Light Bice Green, Plate 17.
*Opening.*—Opens up well; is not affected by adverse weather conditions.

Bloom:
*Size.*—Large. Average size when fully expanded—from 4 to 4½ inches.
*Borne.*—Singly, and several together, and in pyramidal clusters.
*Stems.*—Long; strong.
*Form (when first open).*—High center and full. Permanence—flattens.
*Petalage.*—Double (full but open center). Number of petals under normal conditions—35.
*Color.*—Center of flower—Begonia Rose, Plate 1, with lower half of petals lightly overcast with Scarlet, Plate 1. Outer petals—Geranium Pink, Plate 1, with outer edges of petals lightly overcast with Scarlet-Red, Plate 1. Base of petals (aiglet)—Strontian Yellow, Plate 16. Inside of petals—Geranium Pink, Plate 1, lightly overcast with Scarlet-Red, Plate 1. Reverse of petals—Eosine Pink, Plate 1. General tonality from a distance—Geranium Pink, Plate 1, lightly overcast with Scarlet-Red, Plate 1.
*Discoloration.*—General tonality at end of first day—Geranium Pink, Plate 1, lightly overcast with Scarlet-Red, Plate 1. Second day—Geranium Pink, Plate 1, lightly overcast with Scarlet-Red, Plate 1. Third day—Geranium Pink, Plate 1, with outer edges of petals lightly overcast with Scarlet-Red, Plate 1.

Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; large.
*Persistence.*—Drop off cleanly.
*Fragrance.*—Strong. Nature—tea (average hybrid tea scent).
*Lasting quality.*—On the plant—long. As cut flower—long.

*Genital organs*

Stamens, anthers: Medium size; many; regularly arranged around styles. Color—Cadmium Orange, Plate 3.
Stamens, filaments (threads): Medium length. Color—Begonia Rose, Plate 1.
Pollen: Color—Capucine Buff, Plate 3.
Styles: Columnar; uneven length; medium length; thin.
Stigmas: Color—Light Chalcedony Yellow, Plate 17.
Ovaries: All enclosed in calyx.
Hips: None.
Seeds: None.

*Plant*

Form: Bush.
Growth: Vigorous; upright; bushy.
Foliage: Compound of 5 to 7 leaflets.
*Size.*—Large.
*Quantity.*—Normal.
*Color.*—New foliage: upper side—Oil Green, Plate 5, with outer edges lightly overcast with Carmine, Plate 1; under side—Lettuce Green, Plate 5, lightly overcast with Carmine, Plate 1. Old foliage: upper side—Forest Green, Plate 17; under side—Rainette Green, Plate 31.
*Shape.*—Oval pointed.
*Texture.*—Upper side—leathery. Under side—smooth.
*Ribs and veins.*—Ordinary.
*Edge.*—Serrated (saw-toothed).
*Serration.*—Single; small.
*Leaf stem.*—Color—Kildare Green, Plate 31. Under side—smooth.
*Stipules.*—Medium length; smooth.
Wood:
*New wood.*—Color—Lettuce Green, Plate 5. Bark—smooth.

*Old wood.*—Color—Spinach Green, Plate 5. Bark—smooth.
*Thorns.*—Quantity: on main stalks from base—ordinary; on laterals from stalk—ordinary. Form—narrow base; medium length; hooked downward. Color (when young)—Yellowish Citrine, Plate 16. Position—irregular.
*Prickles.*—Quantity: on main stalks—none; on laterals—none.
*Short needles.*—Quantity: on main stalks—none; on laterals—none.

I claim:

A new and distinct variety of rose plant of the floribunda class, substantially as herein shown and described, characterized particularly as to novelty by the unique combination of a distinctive contrast between the foliage color and flower color, the relatively large size of the flowers, unusual sepals which form a hood over the bud, with one sepal being unusually broad and serrated and the other sepals deeply serrated, and a distinctive Geranium Pink, lightly overcast with Scarlet-Red general color tonality of the flowers.

No references cited.

July 26, 1960 D. H. MOREY, JR Plant Pat. 1,962
ROSE PLANT
Filed Oct. 19, 1959
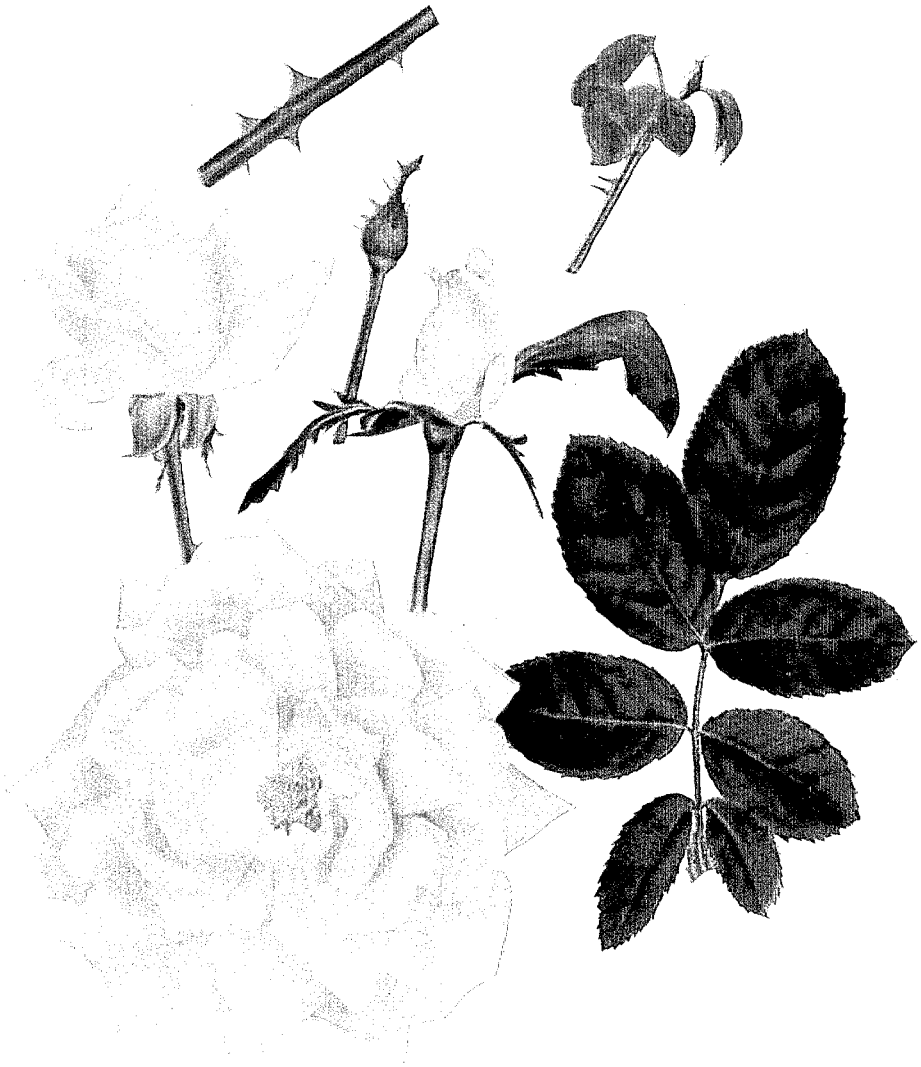
Inventor.
D. H. Morey, Jr.
By: Robb & Robb
Attorneys.